United States Patent
Gilboa

(10) Patent No.: US 8,363,259 B2
(45) Date of Patent: Jan. 29, 2013

(54) METHOD FOR PRODUCING PRINTED PATCHES FOR OPTICAL AND HIGH-CONTRAST GUIDANCE

(75) Inventor: Pinhas Gilboa, Haifa (IL)

(73) Assignee: Activiews Ltd., Haifa (IL)

( * ) Notice: Subject to any disclaimer, the term of this patent is extended or adjusted under 35 U.S.C. 154(b) by 1037 days.

(21) Appl. No.: 12/361,572

(22) Filed: Jan. 29, 2009

(65) Prior Publication Data

US 2009/0290174 A1 Nov. 26, 2009

Related U.S. Application Data

(60) Provisional application No. 61/055,973, filed on May 24, 2008.

(51) Int. Cl.
*G06K 15/00* (2006.01)

(52) U.S. Cl. ...... 358/1.18; 358/1.9; 358/1.12; 358/3.28; 358/540; 600/426; 600/434; 600/556; 600/407; 604/362; 606/116

(58) Field of Classification Search ............... 600/426
See application file for complete search history.

(56) References Cited

U.S. PATENT DOCUMENTS

| | | | |
|---|---|---|---|
| 5,045,080 A * | 9/1991 | Dyer et al. | 604/362 |
| 5,193,106 A | 3/1993 | DeSena | |
| 6,216,029 B1 * | 4/2001 | Paltieli | 600/427 |
| 6,959,711 B2 * | 11/2005 | Murphy et al. | 128/898 |
| 7,127,826 B2 * | 10/2006 | Russell | 33/758 |
| 7,876,942 B2 * | 1/2011 | Gilboa | 382/128 |
| 7,896,816 B2 * | 3/2011 | Utsugi | 600/556 |
| 7,920,909 B2 * | 4/2011 | Lyon et al. | 600/407 |
| 8,108,025 B2 * | 1/2012 | Csavoy et al. | 600/407 |
| 2003/0187458 A1 * | 10/2003 | Carlson, II | 606/116 |
| 2004/0041030 A1 * | 3/2004 | Nimura et al. | 235/468 |
| 2004/0047902 A1 * | 3/2004 | Dupont et al. | 424/449 |
| 2004/0056478 A1 * | 3/2004 | Bruce | 283/81 |
| 2006/0094958 A1 * | 5/2006 | Marquart et al. | 600/434 |
| 2009/0290174 A1 * | 11/2009 | Gilboa | 358/1.9 |

FOREIGN PATENT DOCUMENTS

WO 2007113815 10/2007

* cited by examiner

*Primary Examiner* — Dung Tran
(74) *Attorney, Agent, or Firm* — Mark M Friedman

(57) ABSTRACT

A method is described for producing printed patches to provide a plurality of color markings and high-contrast markings as aligned arrangements of fiducial points. The printed color markings facilitate optical image processing and the printed high-contrast markings facilitate high-contrast image processing. These fiducial points enable a visible area of interest to be located by a person and associated with relevant high-contrast imaging data. This method includes providing a patch; printing at least one arrangement of color markings on the patch; and printing at least one arrangement of high-contrast markings on the patch. According to further features of certain embodiments the markings are aligned, can designate the same point, or can be disjointed.

11 Claims, 8 Drawing Sheets

METHOD FOR PRODUCING PRINTED PATCHES FOR OPTICAL AND HIGH-CONTRAST GUIDANCE

CROSS-REFERENCE TO RELATED APPLICATIONS

This application claims the benefit of provisional patent application Ser. No. 61/055,973 entitled "Methods for Printings Sticker for Guiding System," filed May 24, 2008.

FIELD OF THE INVENTION

The present embodiment generally relates to a method for printing, and in particular, it concerns producing printed patches with aligned color markings and high-contrast markings.

BACKGROUND OF THE INVENTION

Patent application WO2007/113815 titled "System and Method for Optical Positioning and Guidance of a Rigid or Semi-Flexible Tool to a Target" by Pinhas Gilboa, describes an optical guidance system based on a patch attached to the skin of a patient. The patch provides an arrangement of fiducial points. These fiducial points enable a visible area of interest to be located by a person, and associated with relevant imaging data. The optical guidance system coordinates the imaging data with the visible area of interest and provides guidance for a person inserting a medical tool to reach a target that is not directly visible. These fiducial points on the patch include colored markings for optical image processing associated with high-contrast markings for an appropriate imaging system.

In the context of this document, the term colored markings refers to markings that reflect electromagnetic energy in the visible and near-visible spectrums, including the infrared and ultra-violet spectrums. Colors visible to the human eye include the commonly known yellow, blue, red, green, and others. Visible, infrared and ultra-violet colors are detectable by CMOS and CCD technologies. These colors are detectable by an optical imaging system.

High-contrast markings are markings that create sufficient contrast to be readily visible under non-visible imaging techniques such as X-ray and magnetic resonance imaging (MRI). Suitable high-contrast substances that may be used to produce such markings are known in the industry and used in various forms. When a high-contrast radio-opaque substance is placed between a source of appropriate radiation and a surface sensitive to that radiation, the high-contrast substance prevents exposure of specified portions of the sensitive surface. This technique results in the shape of the substance appearing on the resulting image. This image is known as a radiograph. Other radiations can be used for the same process, including gamma rays, Roentgen rays, radium rays, and other nuclear radiation. Radio-opaque imaging systems include X-ray and computerized tomography (CT scan). Similarly, when a high-contrast magnetic substance is used in an MRI scan the shape of the substance appears in the resulting MRI image. Substances such as Gadolinium containing agents and Ultrasmall Supermagnetic Iron Oxide Particles are currently used in the industry. Other imaging techniques include positron emission tomography (PET scan) and fluoroscopy.

It is known that, in color image processing, the color, also known as the tint, should be accurate. The patent application by Gilboa teaches that it is preferable that each of the optical fiducial points is a specific color for easier differentiation by color segmentation. The patent application suggests techniques to produce combinations of color marking and high-contrast markings.

One suggestion is to embed a high-contrast substance in a flat plastic disk and then print color markings on the disk. Preferably, the positions of the markings for the high-contrast imaging system coincide with the optical fiducial points so that the optical fiducial points are directly derived from the scanned data. This device requires the use of two different production techniques. The use of two different production techniques is less preferred than using one production technique because of the additional expense and complexity of production. The resulting plastic disk is also limited in flexibility due to the requirement to embed a substance in the disk. The use of a device that is limited in flexibility is less preferred than using a flexible device because the flexible device can be used in more areas.

A device for marking cutaneous landmarks is disclosed by DeSena in U.S. Pat. No. 5,193,106, X-Ray Identification Marker. This patent teaches the importance of highlighting a visible area of interest with a marker that is easily seen on a radiograph of the internal, or non-visible, related area. The patent also presents techniques to mark an area of interest, converting a visual localization to a radio-opaque localization. One example is a doctor marking a visible area of interest on a patient's body with a visual marking that is also radio-opaque. When the patient is subsequently X-rayed, the visible area of interest that the doctor identified is indicated on the resulting radiograph. This device comprises a black radio-opaque material on an adhesive tape. The purpose of the device is to refer to a visible area of interest on the foot of a patient and enable association of this area with subsequent radiographic imaging data. This device consists of only radio-opaque markings. The device does not suggest a method for color markings and does not provide the precision necessary to guide a rigid or semi-flexible tool to a target.

A possible method for producing high-contrast markings is to use techniques that have been developed for printing electronic printed circuit boards (PCBs). In these techniques, the printing is performed chemically by masking and etching a layer of copper. This technique can be used for producing the high-contrast markings, but is only suitable for printing on substrates that are rigid or semi rigid. Semi rigid substrates have a stiff internal structure that maintains their form. This technique cannot be used for printing on a flexible patch. A flexible patch can be bent without injury or damage.

For printing on flexible materials, a technique such as offset printing or silkscreen printing is preferred. Other techniques such as inkjet printing are also possible. Printing can be done with a dye that is both colored and high-contrast. A dye for printing color high-contrast markings, in the form of a paste or liquid can be prepared by mixing pigment with high-contrast ingredients. For example, to produce high-contrast black dye base suitable for printing, a mix of Lead (Pb) powder in clear liquor can be used. To produce high-contrast white dye base suitable for printing, a mix of Barium Sulfate ($BaSO_4$) in clear liquor can be used. Other heavy metals may also be used to provide high-contrast properties. Adding pigment to these high-contrast pastes results in a colored high-contrast dye.

These dyes may be easily printed using known techniques on rigid or flexible materials. However, the high-contrast ingredients inevitably change the original tint of the pigment. The tint may be lightened because the tint of the ingredients dilutes the color density of the dye, or darkened because the tint of the ingredients thickens the color density of the dye.

The change depends on the color and density of the ingredients used. Accurate color is difficult to achieve with this process.

There is therefore a need for a method to print accurate color markings associated with high-contrast markings. The current embodiment provides such a method.

SUMMARY

In accordance with one embodiment, a method for producing printed patches to provide a plurality of color markings and high-contrast markings includes: (a) providing a patch; (b) printing at least one arrangement of color markings on the patch; and (c) printing at least one arrangement of high-contrast markings on the patch. According to a further feature of certain embodiments, printing the color markings and printing the high-contrast markings designate the same point. According to a further feature of certain embodiments, the printing of the color markings and the printing of the high-contrast markings are aligned. According to a further feature of certain embodiments, the printing of the color markings and the printing of the high-contrast markings are aligned and disjointed. According to a further feature of certain embodiments, the color used is a primary color, other than red. According to a further feature of certain embodiments, the patch is flexible. According to a further feature of certain embodiments, the color markings are printed on a first side of the patch and the high-contrast markings are printed on a second side of the patch opposite to the first side. According to a further feature of certain embodiments, the color markings and the high-contrast markings are printed on the same side of the patch. According to a further feature of certain embodiments, the arrangements of color markings provides a plurality of fiducial points, the fiducial points include a first set of fiducial points and a second set of fiducial points optically distinguishable from the first set of fiducial points, the first set of fiducial points being more closely spaced than the second set of fiducial points. According to a further feature of certain embodiments, the arrangements of markings are configured to delineate a point of penetration of the distal end of a tool.

In accordance with one embodiment, there is provided a method for producing an arrangement of color markings and high-contrast markings wherein each of the colored markings is substantially exactly overlapping with a corresponding high-contrast marking, the method includes: (a) providing a black surface with a given boundary; (b) printing a white high-contrast marking with a given outer boundary wherein the white high-contrast marking is partially overlapping the black surface and the given outer boundary of the white high-contrast marking is within the given boundary of the black surface such that the black surface delimits the boundary of the white high-contrast marking; and (c) printing a transparent color area with a given printed boundary wherein the transparent color area is partially overlapping the white high-contrast marking such that: (i) the given boundary of the transparent color area is outside the given boundary of the white high-contrast marking; (ii) the given boundary of the transparent color area is within the given boundary of the black surface; and (iii) such that the black surface delimits the boundary of the transparent color area.

In accordance with one embodiment, there is provided a method for producing an arrangement of color markings and high-contrast markings wherein each of the colored markings is bounded by a high-contrast marking, the method includes: (a) printing a color area with a given boundary; and (b) printing a black high-contrast marking with a given outer boundary and a given inner boundary wherein the black high-contrast marking is partially overlapping the color area such that: (i) the given outer boundary of the black high-contrast marking is outside the given boundary of the color area; and (ii) the given inner boundary of the black high-contrast marking is within the given boundary of the color area such that the black marking delimits the visible portion of the color area.

BRIEF DESCRIPTION OF FIGURES

The invention is herein described, by way of example only, with reference to the accompanying drawings, wherein.

DETAILED DESCRIPTION

First Embodiment

FIGS. 1, 2A, 2B, 3, 4, 5, 6, 7, 8

The present invention is a method for producing a printed patch that provides a plurality of color markings and high-contrast markings, and a correspond patch. The method begins by providing a patch on which printing can be done. Arrangements of high-contrast markings are printed on the patch and arrangements of color markings are printed on the patch. The order of the printings can be changed, and more than one printing of each type of marking can be used. One embodiment of this method uses multiple printings to create a colored marking that is substantially exactly overlapping the high-contrast marking. An alternate embodiment uses multiple printings to create a colored marking that is bounded by a high-contrast marking. When all of the required arrangements have been printed, the printing of the patch is complete. Additional processing steps may be required to prepare further the patch for the specific application for which the patch will be used.

Figure 1:
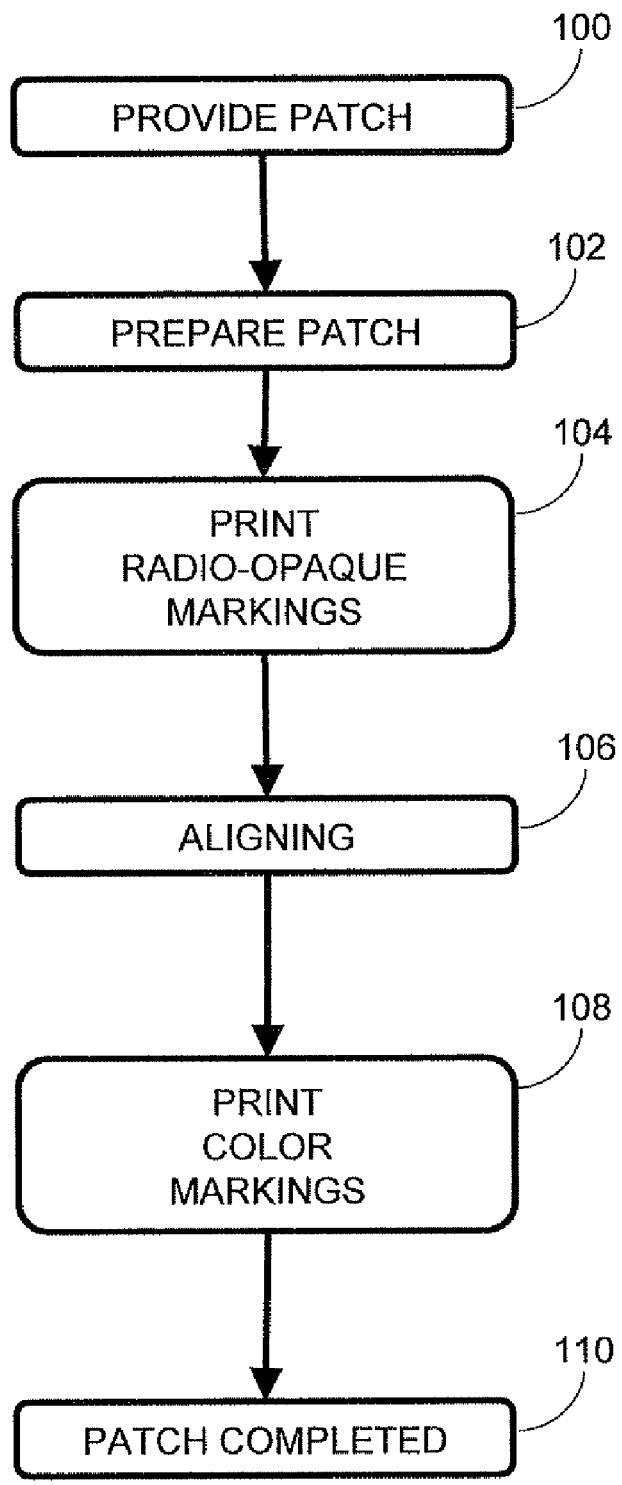
FIG. 1 is a flowchart of a method for printing accurate color markings and high-contrast markings according to the teachings of the present invention.

Referring now to the drawings, FIG. 1 is a flowchart of a method for printing accurate color markings and high-contrast markings. The method of this embodiment begins by providing a patch shown in block 100. The patch is prepared for printing in block 102. High-contrast markings are printed on the patch, shown in block 104. Aligning the printing of the high-contrast markings and the printing of the color markings is shown in block 106. The color markings are printed on the patch, shown in block 108. When all of the required arrangements of high-contrast and color markings have been printed, the patch is completed, as shown in block 110.

Prior to providing the patch for printing, block 100, the patch is designed. The design of a specific patch depends on the specific chosen system configuration for use of the patch. The size of the provided patch depends on the size of the visible area of interest where the patch will be used. A greater distance between markings increases the accuracy of the correlation, so it is generally desirable to use the largest patch that will function in the size of the area of interest. The size of the required patch depends on the viewing angle of the optical imaging system. The minimum size required for the patch depends on the optical imaging system coverage at the minimum distance of the optical imaging system from the patch. The maximum size of the patch depends on the distance the optical imaging system is from the patch in the specific chosen system configuration, and the practical attaching of the patch to the area of interest.

The printed markings are designed to enable use of the patch for the chosen system configuration. Using the method of this embodiment, the markings can be any shape that can be printed but are preferably shaped to facilitate identifying a specific location to be designated by the marking, either at a center of the marking or by some feature, such as a corner, of the marking. Examples of suitable shapes include, but are not limited to, circles, squares, triangles, rectangles, numbers, letters, words, lines, pictures, bar-codes, and arrows.

Printing the color markings is shown in block 108. Accurate color markings are markings that are printed with a color that is uniform and repeatable. A uniform and repeatable color facilitates the identification of the color markings. In principle, an arbitrary color can be printed and then calibrated with the system prior to use, but it is preferable that the color be pre-defined during the process of designing the patch.

Color is the quality of an object or substance with respect to light reflected by the object. In the context of this invention, color includes the colors visible to the human eye and the near-visible spectrums that have a distinctive spectral response, as opposed to black or white that absorbs or reflects all energy in the visible spectrum. The use of colors renders the markings easily discernable during image processing. Colored markings facilitate image processing by color segmentation to identify automatically the colored markings in sampled images. A preferred option is to use colored markings that are visible to the human eye. This process is particularly simplified by the use of primary colors (red, green and blue), although red is problematic in medical applications where soiling by blood may occur. Another option is to use fluorescent markings that are visible under ultraviolet illumination. The chosen system configuration for the patch generates a design that includes specific colors to be used to facilitate color image processing. Achieving accurate color in this embodiment results in the printed color on the patch being substantially exactly the color specified in the design of the patch. Techniques for printing accurate color printing are per se known in the industry. Printing techniques include inkjet, color laser, offset, and silk-screen printing.

Printing the high-contrast markings is shown in block 104. A high-contrast dye for printing high-contrast markings can be created from a variety of substances. Depending on the specific substances used to create the dye, the dye will have a tint. One example is to use a mix of Lead (Pb) powder in clear liquor to produce a high-contrast black dye base suitable for printing. Another example is to use a mix of Barium Sulfate (BaSO4) in clear liquor to produce a high-contrast white dye base suitable for printing. Other combinations are well known in the industry. The tint of the dye can be used to help construct a marking design on the patch. One example is to use a black high-contrast dye to mask the boundary of a color marking. Masking in this context refers to the use of light absorbance of a first dye to hide, or at least reduce the visibility of, the color of a second dye in a selected area of overlap. Embodiments using these features are described in reference to FIG. 6 and FIG. 7. It should be noted that for color image processing the preferred markings are the accurate color markings. The high-contrast markings can be used for image processing, for example, providing a geometrically well-defined outline to a marking, but they do not provide the accurate color necessary for differentiation by color segmentation.

Printing the color markings is a separate step from printing the high-contrast markings. The order of the steps is non-limiting. More than one printing of each type of marking is possible and the printings can be done in any order, unless otherwise specified. As an example, refer to FIG. 1, where preparing the patch in block 102, can be followed by printing color markings in block 108, and then followed by printing the high-contrast markings, block 104. Preparing the patch can include a variety of steps, depending on the chosen system configuration for use of the patch, including: Cutting the raw patch material to the size necessary for printing, cleaning the patch material, preparation of the printing surface, and pre-treating the material of the patch. The markings can be printed anywhere on the patch, to include printing on top of other markings and to include printing on opposite sides of the patch. High-contrast markings can be separately printed on top of color markings, and color markings can be separately printed on top of high-contrast markings. Multiple layers of marker printing can be used to construct specific designs on the patch. Further embodiments using this process will be described.

Figure 2A:
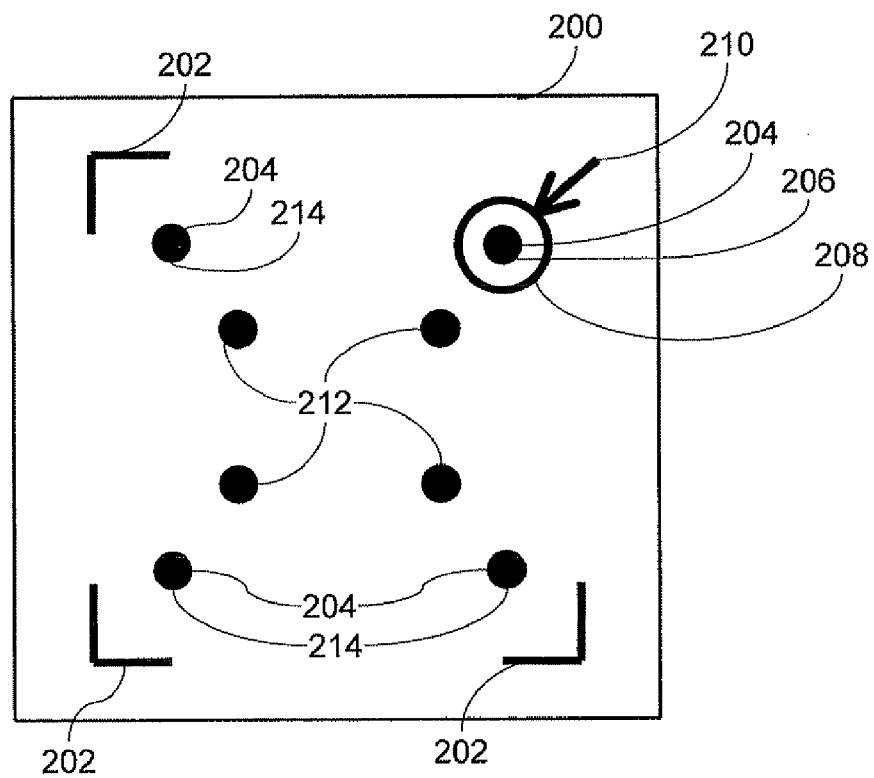
FIG. 2A is a plan view of a printed patch according to an embodiment of the present invention.
Figure 2B:
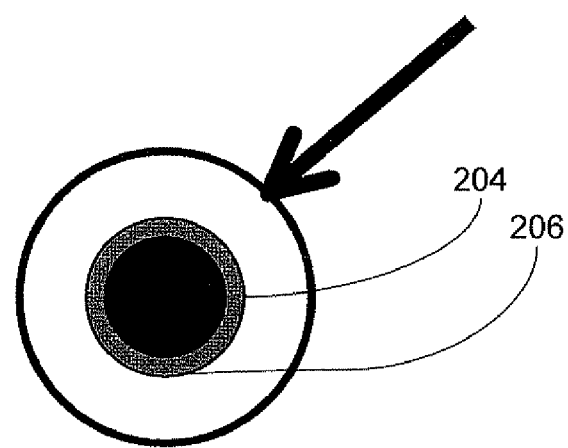
FIG. 2B is an enlarged view of one of the markings from the printed patch of FIG. 2A.

FIG. 2A is a plan view of a printed patch 200. The patch has markings 202, 204, 206, 208, 210, 212. Markings 204 and 206 designate the same point. Referring to FIG. 2B which is an enlarged view of one of the markings from the printed patch of FIG. 2A. The color marking 206 is printed on top of the high-contrast marking 204. Note that the difference in scale between the markings is for illustration. Both marks designate the same point on the patch. Refer to FIG. 2A where high-contrast markings 204 are aligned with the colored markings 212. Aligned in this context refers to the position of the markings on the patch being pre-designated during the design of the patch and the printing of the markings has a known, repeatable spatial relationship. Aligning printed markings results in their physical position arranged in the desired position. In principle, the high-contrast markings could be arbitrarily printed on the patch, and then calibrated with the color markings by a sufficiently powerful processing system prior to use. This post-printing calibration is possible, but it is preferable that the position of the color markings and the position of the high-contrast markings color be pre-defined during the process of designing the patch.

Referring to FIG. 2B, the color marking 206 is visible to an optical imaging system which can determine the location of the marking, and the location of the high-contrast marking 204 is known from the high-contrast image data. Coordinating the locations of the color marking and high-contrast marking can be done by known techniques, such as correlating the center of mass of their images. This coordination designates the same point on the patch. Note that since the markings are aligned, the relationship between the markings is known and the markings can be used in a variety of ways to designate a point on the patch. Further examples are described elsewhere in relation to FIG. 3.

Refer to FIG. 1 where in the method for printing includes a step, shown in block 106 for aligning the printings. This aligning step facilitates printing the arrangement of markings in the desired position. Techniques for aligning multiple printings per se are known in the industry. Techniques for aligning multiple printings include using a common print carriage with multiple print heads, mechanically aligning the printer to a physical reference of the patch such as the side of the patch, scanning the patch for a known optical reference feature from a previous printing to align a current printing, examining the alignment of the markings using back-lighting/light table techniques, changing the limiters that align the paper on the vacuum table on which the printing mesh is attached, and any other technique for aligning multiple printings. Aligning the color markings with the high-contrast markings facilitates coordinating the visible area of interest with the high-contrast imaging data. This further facilitates the optical guidance system providing guidance to a person, for example, as described in the above-referenced WO2007/113815.

Markings may be printed in a variety of arrangements. In FIG. 2B color marking 206 and high-contrast marking 204 are substantially exactly overlapping. The boundary of the high-contrast marking is preferably slightly smaller, approximately 0.1 millimeter (mm) than the boundary of the color marking. This technique facilitates registration of the markings to be substantially exactly overlapping. In FIG. 2A the arrangement of color markings 204 are aligned with the high-contrast markings 212, but the markings are disjointed. In other words, markings 204 and 212 are in a known relationship to each other, but do not overlap.

Figure 3:
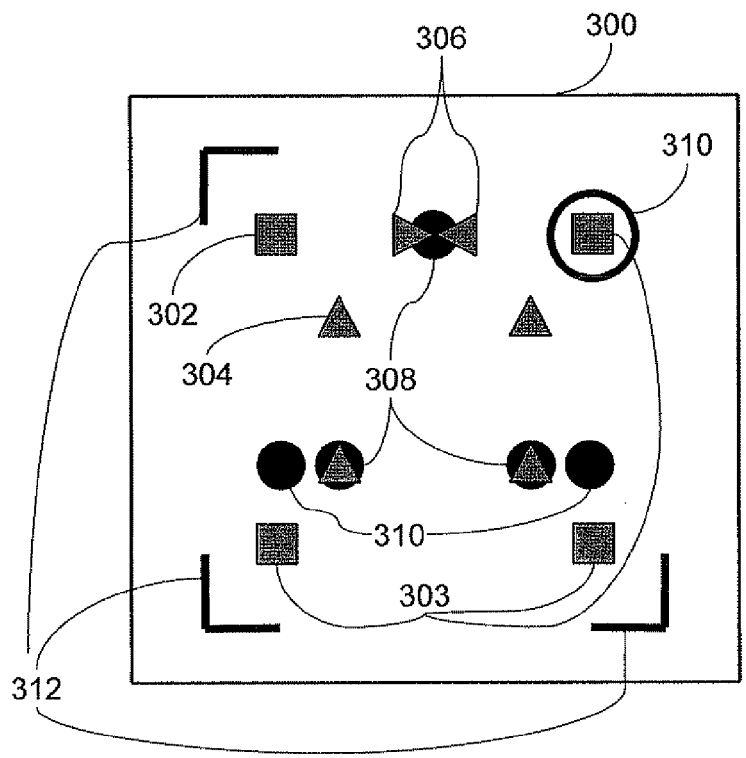
FIG. 3 is a plan view of a printed patch according to an implementation of the present invention with a variety of markings.

Referring to FIG. 3 is a plan view of a printed patch 300 with a variety of markings. The shapes of the markings facilitate use of the patch to meet the specific requirements of the chosen system configuration. The markings can be any shape that can be printed, but are preferably shaped to facilitate identifying a specific location. Markings can also provide general information and specific instructions for the user. Colored marking 302 is a square and can be used to designate a single location on the patch, or in conjunction with other squares 303 can form a larger virtual shape, or direct a person to an area of interest. Colored marking 304 is a triangle and can be used to designate a single location. Colored markings 306 are two triangles with their apexes touching. This configuration of markings 306 can be used to facilitate identifying a specific point on the patch where the apexes touch. Colored markings can be printed with a space between them to designate the space between the two markings as the point of interest. High-contrast markings 308 are printed on the patch substantially-aligned with the corresponding color markings. High-contrast markings 310 are printed on the patch aligned in a known special relationship with the colored markings and disjointed from the color markings. These descriptions of markings are intended only to serve as examples and many other embodiments are possible.

Referring to FIG. 2A, there is shown an example of the use of an arrow shaped marking 210 to facilitate directing the user to an area on the patch. Use of markings such as the arrow 210, or the circle 208, are used to provide a visible reference area for the user. The framing markings 202 appear in three of the four corners of the printed patch. The framing markings can be used to facilitate an optical guidance system determining the orientation of the patch.

Markings can also be used to add graphical information for directing the user where to perform certain operations. An example is shown in FIG. 2A where an arrow 210 is printed with the arrow tip adjacent to a circle 208. The circle 208 surrounds another circle 206. This arrangement of markings facilitates the user first locating the corner with marking 206 instead of the other circle markings 214 in the other corners of the patch. The arrow 210 and circle 208 direct the user to an area on the patch regardless of the rotation of the patch. This area provides a known starting point for using the patch with, for example, an optical guidance system. The known starting point facilitates the coordination of the high-contrast imaging data with the visible area of interest and provides guidance for a person.

One embodiment of the color markings is to print them using a primary color. A primary color is a color that primarily stimulates a given optical sensor in the range that the sensor is sensitive to interpret that color. An example is printing a color sufficiently close to blue, to provide a response of the sensors that the color is blue. The primary colors are generally referred to as red, green and blue. Note that in medical applications where the patch may be soiled by blood, red may be problematic and therefore use of blue and green only is preferred.

A further embodiment is the use of a flexible patch. A flexible material can be deformed without injury or damage. A flexible patch is able to conform to an area of interest. An example of the need for a flexible patch is on the leg of a person. Human legs are generally curved. For a better fit, a flexible patch can conform to the shape of the area of interest on the leg. Deforming with movement avoids the patch breaking and avoids the patch disengaging from the person. This printing method can be used for printing on flexible materials and for printing on substrates that are rigid or semi rigid.

Figure 2C:
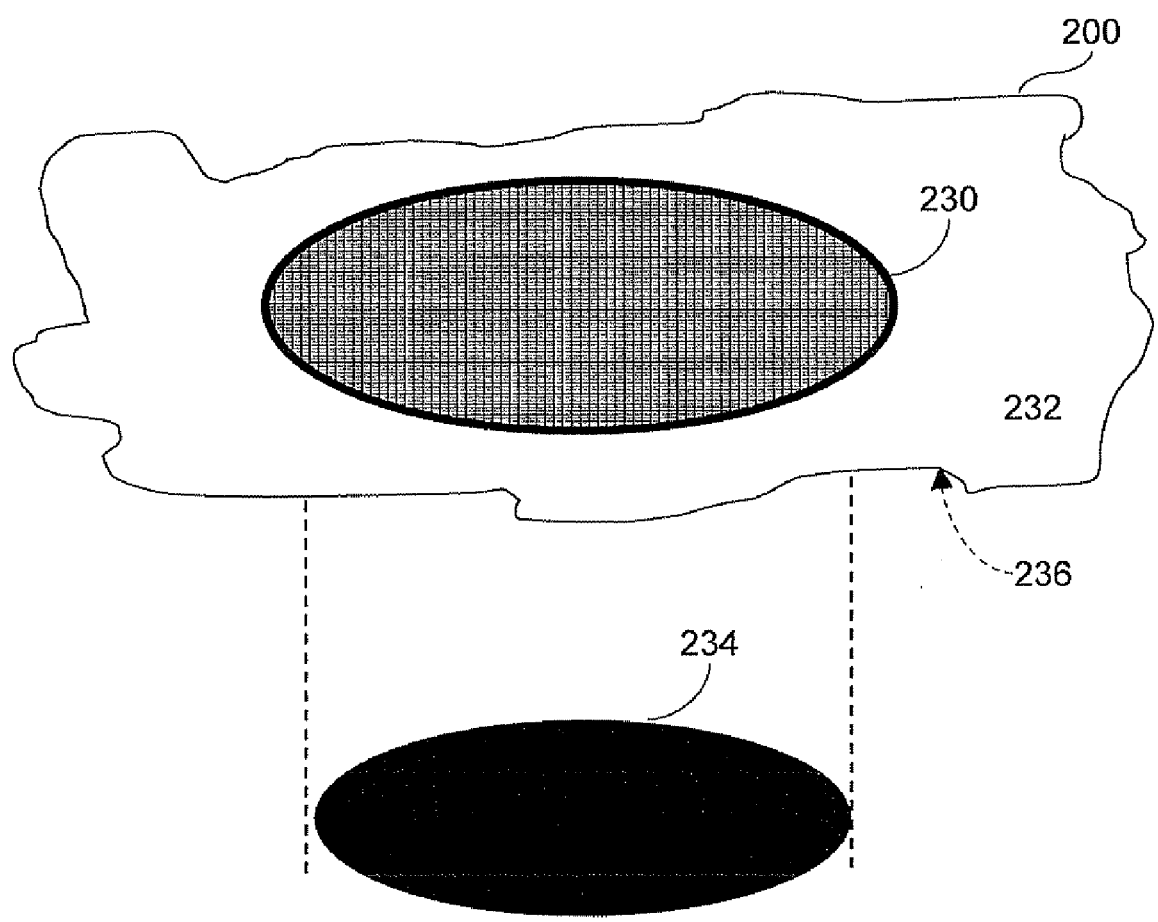
FIG. 2C is a schematic representation of a marking according to an implementation of the present invention in which the marking includes components applied on opposite sides of a patch.

An alternate embodiment of the printed patch is to print the color markings on one side of the patch and to print the high-contrast markings on a second side of the patch opposite to said first side. Referring to FIG. 2C a schematic representation of a marking in which the marking includes components applied on opposite sides of a patch, a patch 200 is provided. A color marking 230 is printed on a first side of the patch 232 and a high-contrast marking 234 is printed on the second side of the patch 236. As described previously, the order of the printing and number of printings is non-limiting on each side of the patch.

Another embodiment of the printed patch is to print the color markings and the high-contrast markings on the same side of the patch. Refer to FIG. 2B as an example of a high-contrast marking 204 and a color marking 206 printed on the same side of the patch. The order of the printing and number of printings is non-limiting on each side of the patch.

Figure 4:
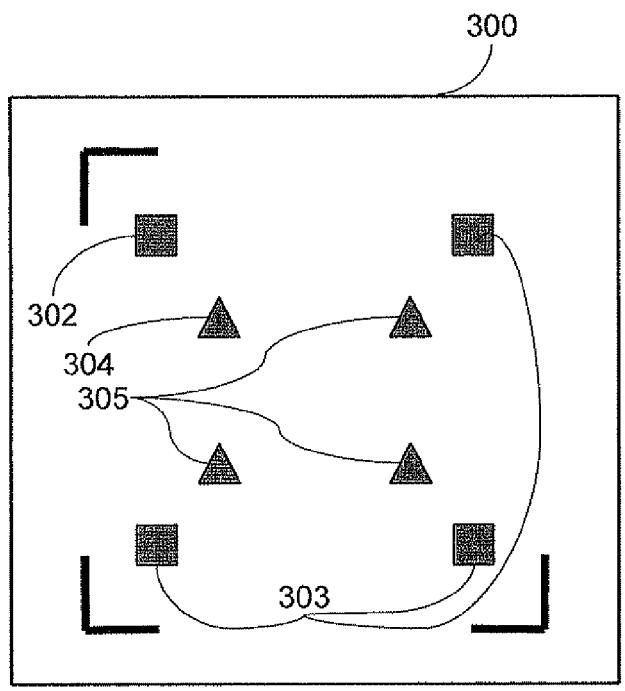
FIG. 4 is a plan view of an alternative implementation of a printed patch according to the present invention with a variety of markings.

Referring to FIG. 4, a plan view of an alternative implementation of a printed patch with a variety of markings. The printed patch has a variety of printed markings providing a plurality of fiducial points. The arrangement of color markings 302, 303 provides a first set of fiducial points. The arrangement of color markings 304, 305 provides a second set of fiducial points that is more closely spaced than the first set of fiducial points 302, 303.

Figure 5:
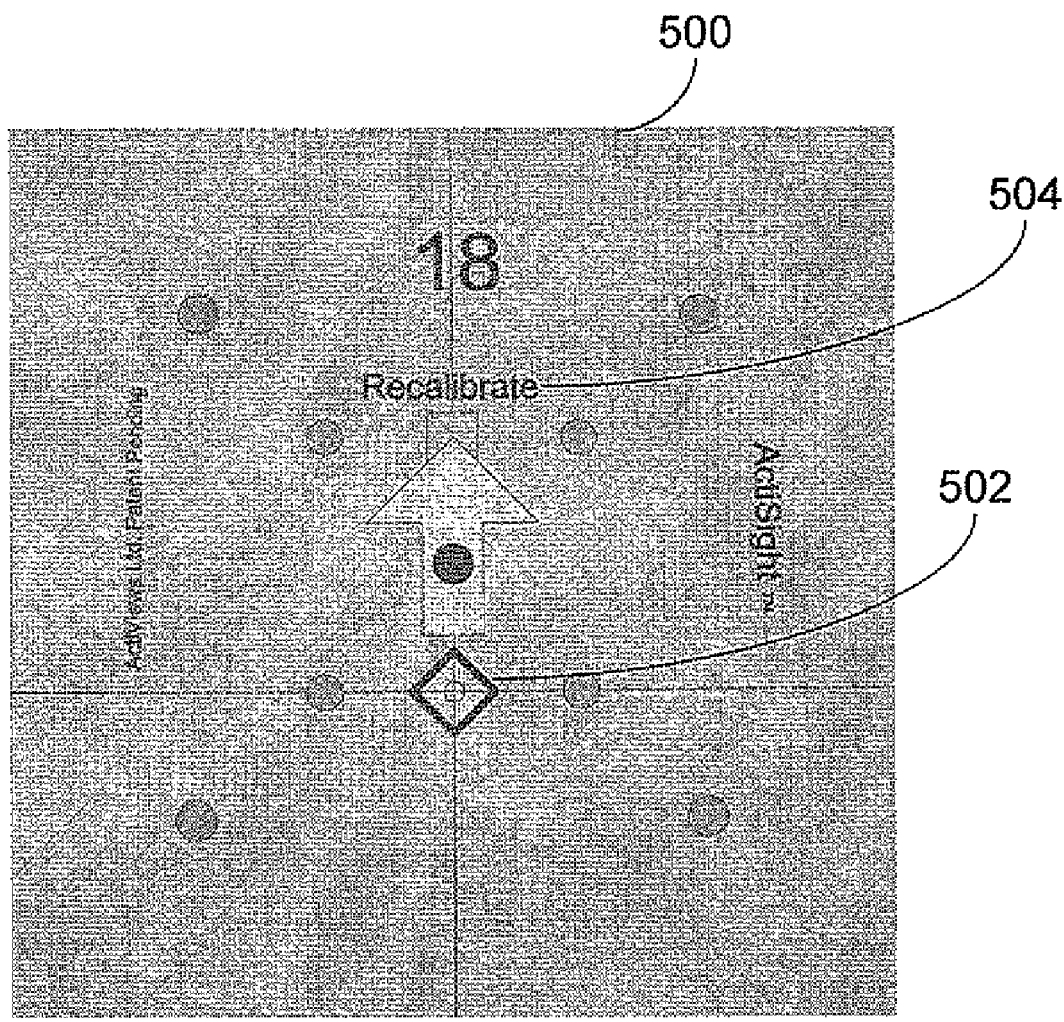
FIG. 5 is a photograph of a printed patch according to an implementation of the present invention.

The markings can be used to delineate a point of penetration of the distal end of a tool. Refer to FIG. 5 a photograph of a printed patch 500. The markings in the center of the patch 502 provide a visible reference area for the user to insert the distal end of a tool. In this embodiment, the tool penetrates the patch at the visible marking.

An additional optional feature is to use the markings to designate certain locations on the patch as control locations associated with specific system functions. Referring to FIG. 5, the marking "Recalibrate" 504 designates a control location on the patch. A user of the system brings the distal end of a tool into contact (or close proximity) with one of the control locations. The monitoring system detects this contact (or close proximity) and performs the corresponding allocated system function. Examples of system control functions that may be allocated to locations on the patch in this manner include, but are not limited to initiating tool length recalibration, changing display modes or other parameters of the display, inputting any other real-time data or changing any other operational parameter of the system, and power-off. The use of touching the tool against a location on the patch as a user interface input is particularly advantageous since it avoids the need for the system operator to touch any other equipment or distract his or her attention from the area of interest.

Figure 8:
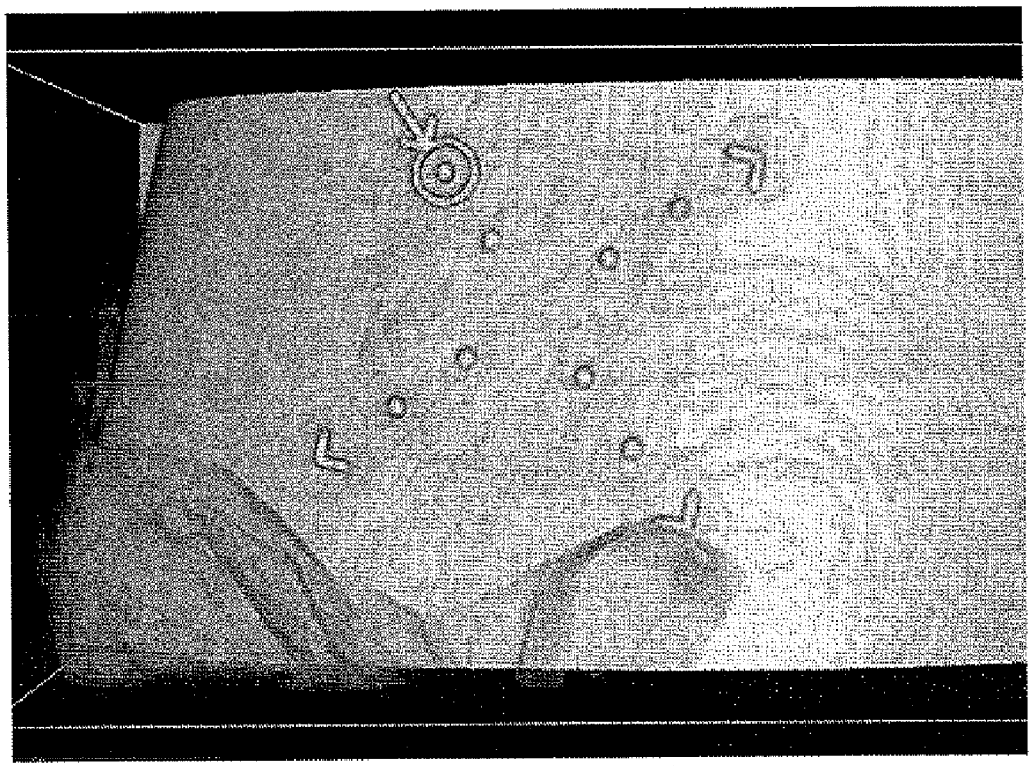
FIG. 8 is an image of a patch on the skin of a person.

Referring to FIG. 8 an image of a patch on the skin of a person. This image is a computerized tomography (CT scan) of the limb of a person. A printed patch that provides a plurality of color markings and high-contrast markings was attached to the skin of the person to designate an area of interest. The various high-contrast markings that were printed on the patch are visible in the resulting image. These markings direct the attention of the user and provide coordination between the visible area of interest and the high-contrast image information.

Figure 6:
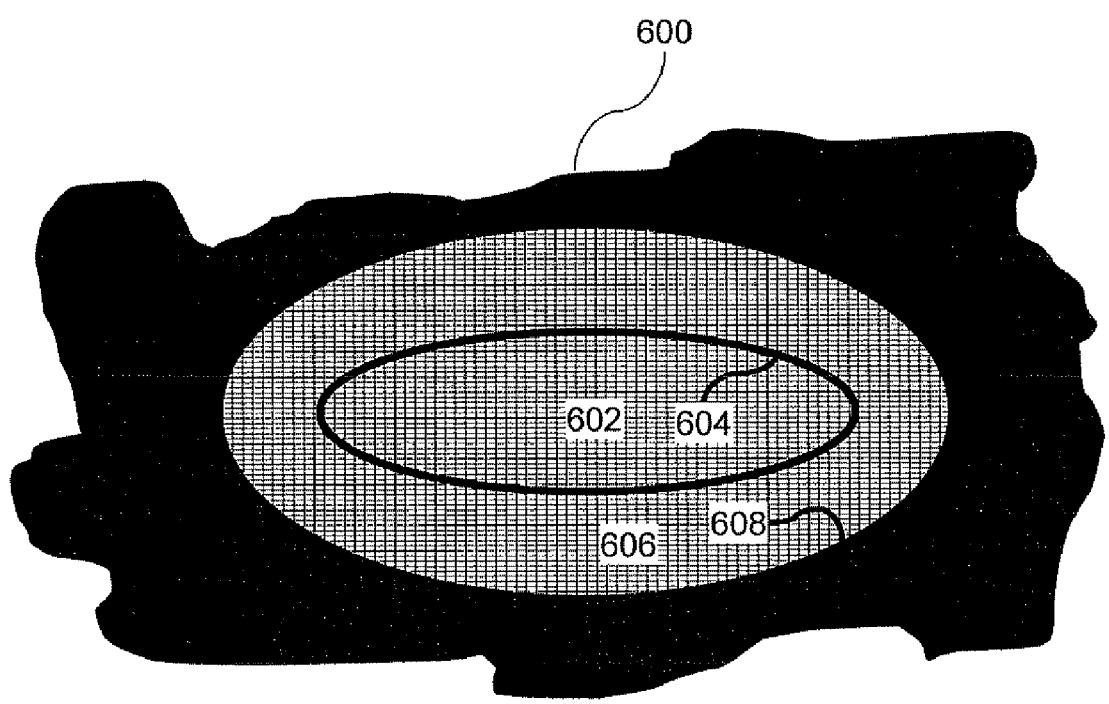
FIG. 6 is a schematic representation of a color marking, according to an implementation of the present invention, which is substantially exactly overlapping a corresponding high-contrast marking.

In an alternate embodiment, referring to FIG. 6, a schematic representation of a color marking that is substantially exactly overlapping a corresponding high-contrast marking. This method begins by providing a black surface with a given boundary 600. The black surface can be provided by a variety of ways, for example, an area of black can be printed on a white patch. Another example of a black surface is providing a black patch. The black printed area can work with this method even if it is not a contractible planar region, as long as the alignment of printings is designed for this situation.

The next step is to print a white high-contrast marking 602 with a given outer boundary 604, so that the white high-contrast marking is partially overlapping the black surface. The outer boundary 604 of the white high-contrast marking is within the boundary of the black surface. Next, a transparent color area 606 with a given printed boundary 608 is printed so that it is at least partially overlapping, and typically completely overlapping, the white high-contrast marking 602. The boundary of the transparent color area 608 is outside the given boundary of the white high-contrast marking 604 and the boundary of the transparent color area 608 is within the given boundary of the black surface 600. Thus, the black surface masks the transparent color 606 outside of the boundary of the white-high-contrast marking 604. This printing method facilitates the transparent color covering the white high-contrast marking. When light is filtered through the transparent color, it is reflected by the white high-contrast marking. The reflected light is the transparent color. Generally, the result of this method is a colored marking that is substantially exactly the same shape and position as the corresponding high-contrast marking.

Figure 7:
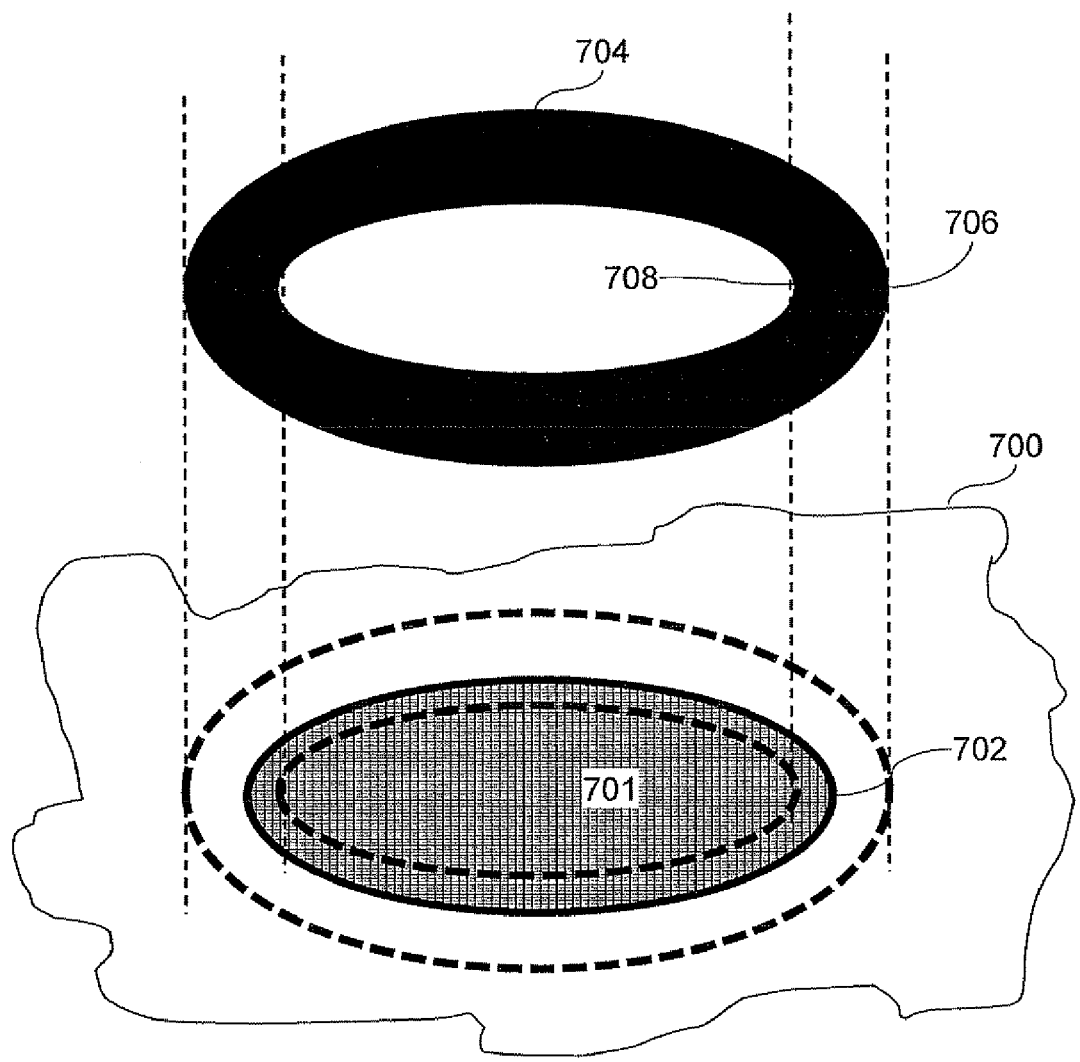
FIG. 7 is a schematic representation of a high-contrast marking bounding a color marking, according to an implementation of the present invention.

In an alternate embodiment, referring to FIG. 7 a schematic representation of a high-contrast marking bounding a color marking. The method begins by printing on a patch 700 a color area 701 with a given boundary 702. Next, a black high-contrast marking 704 with a given outer boundary 706 and a given inner boundary 708 is printed so the black high-contrast marking is partially overlapping the color area. The given outer boundary of the black high-contrast marking 706 is outside the given boundary of the color area 702 and the given inner boundary 708 of the black high-contrast marking is within the given boundary of said color area 702. The black marking delimits the visible portion of the color area 701. Generally, the result of this method is that only the portion of the color area that is seen inside the inner boundary of the black high-contrast marking is visible.

One use of this embodiment is to facilitate an optical tracking system to coordinate the visible are of interest denoted by the color marking with radio-imaging data. Because only the portion of the color marking seen inside the inner boundary of the black high-contrast marking is visible to the optical imaging device, the detection of the color marking can be used in coordination with the known alignment of the corresponding high-contrast marking to coordinate the location of the area of interest, and subsequently guide a user as necessary.

It will be appreciated that the above descriptions are intended only to serve as examples, and that many other embodiments are possible within the scope of the present invention as defined in the appended claims.

What is claimed is:

1. A method for producing printed patches to provide a plurality of color markings and high-contrast markings, comprising:
   (a) providing a patch;
   (b) printing at least one arrangement of color markings on said patch wherein said color markings are detectable under illumination from at least one wavelength of electromagnetic energy in the visible or near-visible spectrums; and
   (c) printing at least one arrangement of high-contrast markings on said patch wherein said high-contrast markings create contrast that is readily visible under non-visible imaging techniques
   wherein the arrangements of color markings provide a plurality of fiducial points, said fiducial points including a first set of fiducial points and a second set of fiducial points optically distinguishable from said first set of fiducial points, said first set of fiducial points being more closely spaced than said second set of fiducial points.

2. The method of claim 1 wherein said printing of said color markings and said printing of said high-contrast markings designates the same point.

3. The method of claim 1 wherein said printing of said color markings and said printing of said high-contrast markings are aligned.

4. The method of claim 3 wherein said printing of said color markings and said printing of said high-contrast markings are disjointed.

5. The method of claim 1 wherein the color used is a primary color, other than red.

6. The method of claim 1 wherein said patch is flexible.

7. The method of claim 1 wherein said color markings are printed on a first side of said patch and said high-contrast markings are printed on a second side of said patch opposite to said first side.

8. The method of claim 1 wherein said color markings and said high-contrast markings are printed on the same side of said patch.

9. The method of claim 1, wherein the arrangements of markings is configured to delineate a point of penetration of the distal end of a tool.

10. The method of claim 1 wherein a color of the color markings is selected from the group consisting of visible, infrared and ultra-violet.

11. The method of claim 1 wherein said high-contrast markings are selected from substances selected from the group consisting of radio-opaque and magnetic.

* * * * *